United States Patent [19]

Carmichael et al.

[11] Patent Number: 4,576,151

[45] Date of Patent: Mar. 18, 1986

[54] ORTHOPEDIC LEG APPLIANCE

[76] Inventors: Hoagy C. Carmichael, Box 877, Whitefish, Mont. 59937; Miles R. Schooler, 250 Brenner Rd., Columbia Falls, Mont. 59912

[21] Appl. No.: 591,502

[22] Filed: Mar. 19, 1984

[51] Int. Cl.[4] .............................................. A61F 3/00
[52] U.S. Cl. ................................ 128/80 C; 128/80 B; 128/80 F; 128/80 R
[58] Field of Search .................. 128/80 R, 80 A–80 J

[56] References Cited

U.S. PATENT DOCUMENTS

| Re. 30,501 | 2/1981 | Almeida | 128/80 C |
|---|---|---|---|
| 1,585,828 | 5/1926 | Bierig | 128/80 |
| 2,545,843 | 8/1949 | Cohan | 128/80 |
| 2,690,176 | 9/1954 | Nelson | 128/80 |
| 2,963,020 | 5/1958 | Moran | 128/80 |
| 3,055,359 | 2/1959 | Palmer | 128/80 |
| 3,086,522 | 4/1963 | Frohmader | 128/80 |
| 3,171,407 | 2/1965 | Rogers | 128/80 |
| 3,304,937 | 2/1967 | Callender, Jr. | 128/80 |
| 3,805,773 | 4/1974 | Sichau | 128/80 E |
| 3,958,567 | 5/1976 | Callender, Jr. | 128/80 R |
| 4,088,130 | 5/1978 | Applegate | 128/80 F |
| 4,243,027 | 1/1981 | LaCourse | 128/80 F |
| 4,303,065 | 12/1981 | Ericson | 128/80 A |
| 4,336,795 | 6/1982 | Nichols | 128/80 A |

Primary Examiner—Curtis R. Davis
Attorney, Agent, or Firm—Wells, St. John & Roberts

[57] ABSTRACT

A orthopedic leg appliance includes opposed pairs of cuff members that may be attached a patient's legs and adjusted relative to one another to apply torsional forces to the upper legs. The appliance includes two pairs of cuff members. First cuff members are mountable to the patient's upper legs while lower cuff member mount to the lower legs. The cuff members are held by knee hinge mechanisms for a free pivotal movement between selected limits. A cross member extends between the cuff pairs and includes torsional adjustment mechanisms and breakaway hinge mechanisms. The torsional adjustment mechanisms allow for selected torsional settings of the cuff members to apply rotational forces to the patient's legs. The breakaway hinge mechanism facilitates relative pivotal motion of the cuff pairs toward and away from one another between operative and inoperative positions without affecting the torsional settings. The inoperative position facilitates mounting and dismounting of the cuff members to the patient's legs. In the operative position, the hinge is locked and the cuffs can be turned to apply torsional corrective forces to the legs.

20 Claims, 16 Drawing Figures

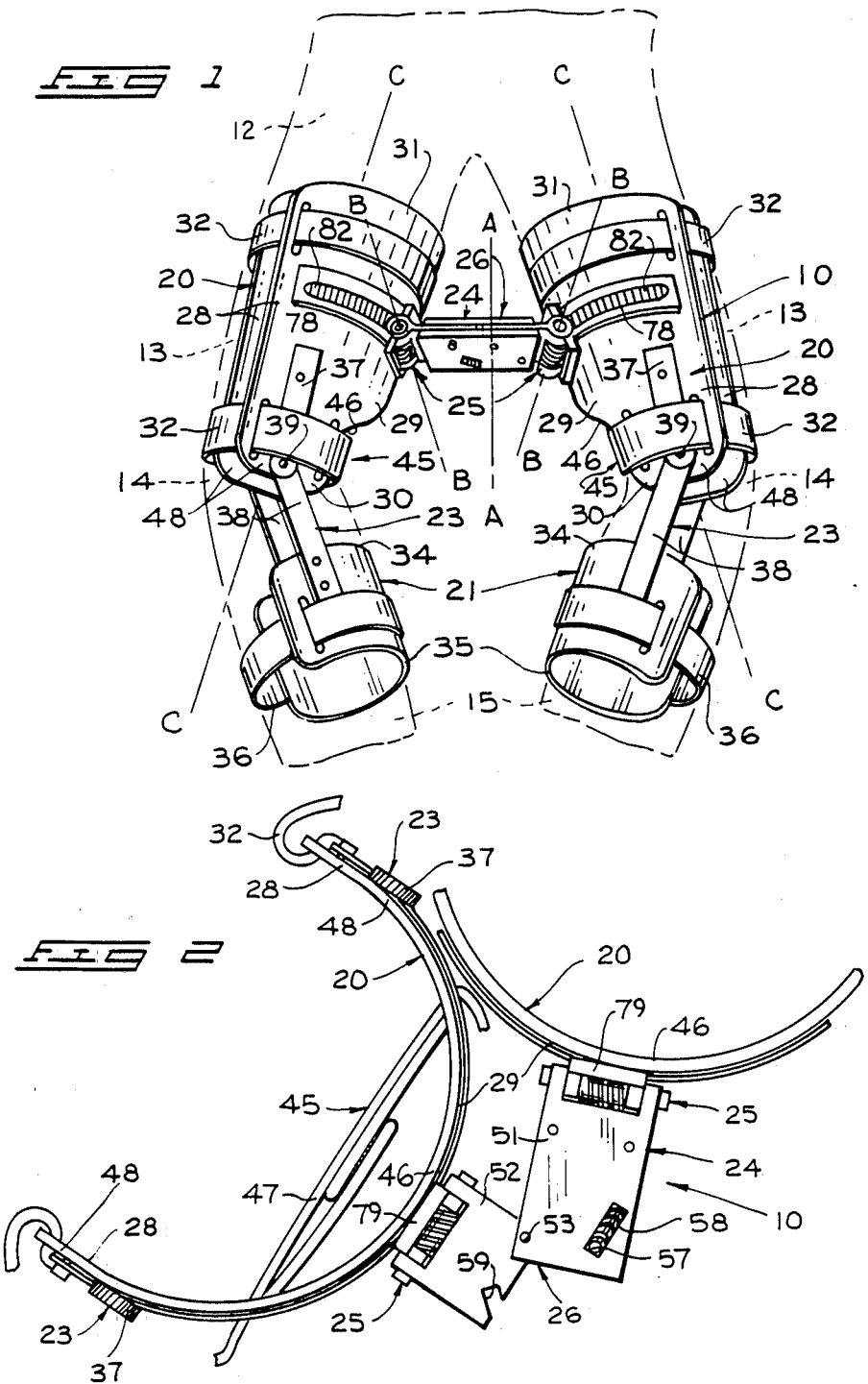

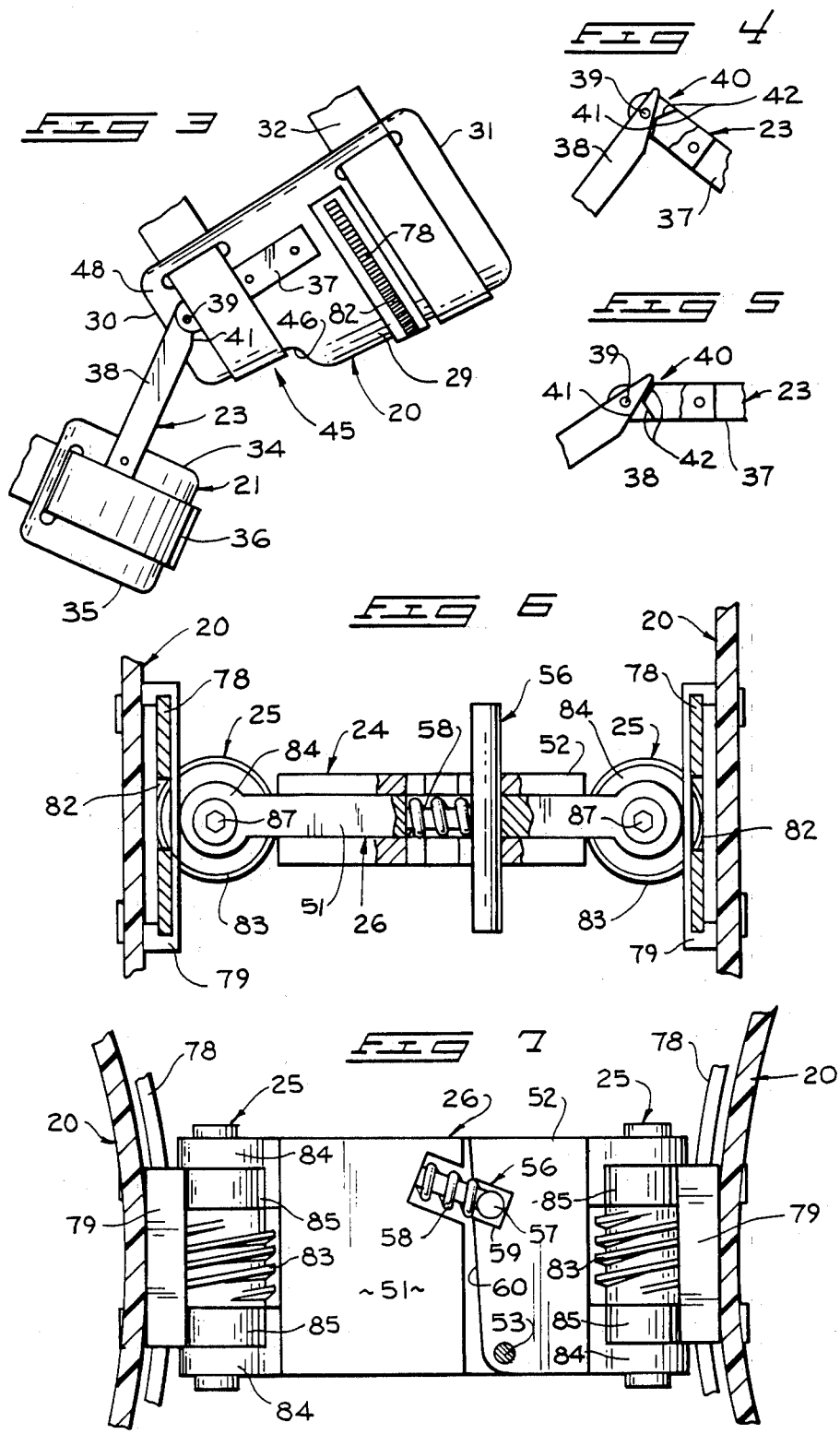

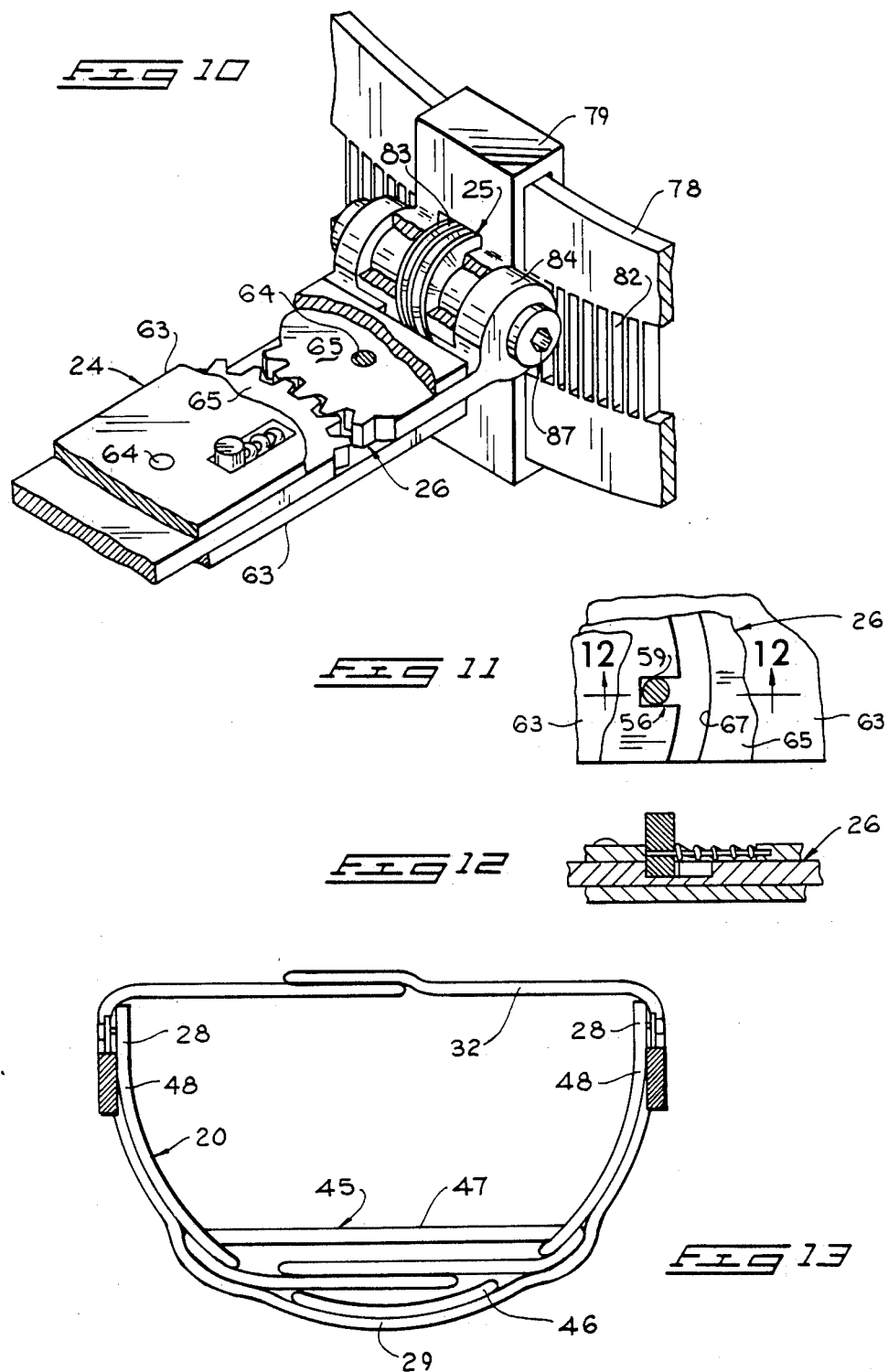

ORTHOPEDIC LEG APPLIANCE

FIELD OF THE INVENTION

The present invention relates to orthopedic correction of lower limbs of the human body, particularly through application of femoral torsion.

BACKGROUND OF THE INVENTION

It has been somewhat recently discovered that many supposed leg and foot deformities are really caused by hip joint problems. For example, in-toedness may well be caused by internal femoral torsion rather than tibial torsion. However, many corrective appliances are still designed to correct the problem by applying corrective torsional forces through the feet. This is often done via a transverse "Dennis Brown" bar with outwardly pivoted shoes mounted to the bar ends. The patient's feet are placed in the shoes which, are then turned to apply torsional forces to the lower legs. If the problem is actually in the hip, correctional forces at the feet are usually insufficient to place the hip under sufficient corrective strain. Further, the forces applied to the hip joint must be transferred through the knee. It is not uncommon for individuals having been exposed to such corrective procedures to later develop knee problems.

U.S. Pat. Nos. 4,336,795; 2,963,020; and 4,303,065 all deal with forms of the "Dennis Brown" bar, making use of shoes or other attachments mounted at the outward ends of elongated bars for selectively turning the wearer's feet in or outwardly. These apparatus function well for a correcting problems that may be alleviated by applying tibial torsion. However, they are not nearly so effective for correcting hip rotational problems. It has therefore becomes desirable to obtain some form of apparatus by which fibular rotation may be used to more directly correct hip rotational problems without interfering with or applying unnecessary forces to the knee or ankle joints.

U.S. Pat. No. 3,815,589 to Bosley discloses a brace assembly for controlling hip rotation in a child. This device represents a direct approach to the hip rotational problem by providing a brace mechanism that works both legs against one another and against "suspender" straps that extend from the brace upwardly around the wearer's shoulders. This device is intended primarily for correcting very early hip deformation in children. Adjustments are possible by use of cuff members that are slidably attached to leg frames. The cuff members will slide in an arch to facilitate adjustment of the amount of torsion desired to be applied to the child's legs. One cuff is intended to be mounted to the child's upper leg, while the remaining cuff fits the lower leg. Both pairs of cuffs are joined by a rigid center connector.

While the Bosley brace assembly represents a more direct approach to the hip rotation problem, it does not do so without certain difficulties. Firstly, the adjustments are preferably made by a doctor, therapist, or other knowledgeable person who properly understands the correct adjustments for applying correct amounts of torsional forces to the wearer's legs. Thus, the adjustments are made periodically and the positions are set and remain between adjustments. The child's legs must be fitted to the preset cuff members. This is a very frustrating procedure for the person who must force the child's legs into awkward positions. It is even more discomforting for the child who must be subjected to this discomfort whenever the brace mechanism is to be attached or dismounted. This procedure occurs frequently since such braces are often used only at night time.

U.S. Pat. No. 3,958,567 discloses a substantially improved apparatus for applying tibial torsion without substantially involving the knee joint. This device includes an angular cuff arrangement by which the upper leg of the patient is gripped as well as the lower leg with the knee in between. The knee is held at an angle by the cuff arrangement. A torsion applying cuff then fits over the wearer's shoe to apply rotational forces directly to the tibia. A somewhat similar appliance is shown in the 1963 patent (U.S. Pat. No. 3,086,522) to Frohmaderf and an earlier patent (U.S. Pat. No. 3,304,937) to Calender, Jr.

U.S. Pat. No. Re. 30,501 to Almeida discloses a universal knee orthosis that includes a pivoted pair of cuffs used to prevent hyper-extension of the wearer's leg and, generally to limit flexural motion of the knee joint. The device is not intended for use in applying torsional forces to the wearer's leg. Similar apparatus is disclosed in the 1962 Patent to Palmer (U.S. Pat. No. 3,055,359); a leg brace structure shown in the 1954 Patent to Nelson (U.S. Pat. No. 2,690,176); the hinged joint for leg braces shown in the 1951 patent to Cohan (U.S. Pat. No. No. 2,545,843); an orthopedic device disclosed by Bierig (U.S. Pat. No. 1,585,828); the hinge for knee brace disclosed by Applegate (U.S. Pat. No. 4,088,130); the brace structure shown by Sichau (U.S. Pat. No. 3,805,773); and U.S. Pat. No. 3,171,407 to R. D. Rogers which shows an orthopedic foot brace of a type used to simply brace the wearer's foot or set angulation of the foot relative to the tibia.

U.S. Pat. No. 4,243,027 to LaCourse discloses a hip stabilizer. This device makes use of a rigid metallic frame set about the wearer's lower torso to control movement of the individual's legs and to promote normal muscular development. The device includes adjustable features that adapt the apparatus to different leg lengths. The device can be applied to the hips and legs to control motions of the legs and in walking. It is not intended to place the legs under torsional forces or to correct deformities but merely to hold the legs in normal orientation to facilitate walking and "normal" muscular development.

BRIEF DESCRIPTION OF THE DRAWINGS

The present invention is illustrated in the accompanying drawings in which:

FIG. 1 is a pictorial view of the present appliance mounted to the legs of a patient, the patient being shown partially and in phantom lines;

FIG. 2 is a fragmented enlarged plan view of the present appliance in an inoperative position to facilitate mounting and dismounting to a patient's legs;

FIG. 3 is a side elevation view of a single cuff arrangement for the present appliance;

FIG. 4 is a fragmented view illustrating one position of the hinged mechanism for the present appliance;

FIG. 5 is a view similar to FIG. 4 only different operational position of the hinged components;

FIG. 6 is an enlarged fragmentary view of a breakaway hinge mechanism for the present appliance;

FIG. 7 is a plan view as seen from above in FIG. 6;

FIG. 10 is a fragmented pictorial view illustrating another form of the breakaway mechanism;

FIG. 11 is a fragmented top view of a pin release mechanism for the breakaway hinge shown in FIG. 10;

FIG. 12 is a sectional view taken substantially along line 12—12 in FIG. 11;

FIG. 13 is an enlarged end view of a lower cuff for the present appliance illustrating a knee hinge access positioning feature thereof;

DETAILED DESCRIPTION OF THE PREFERRED EMBODIMENT

Figure 8:
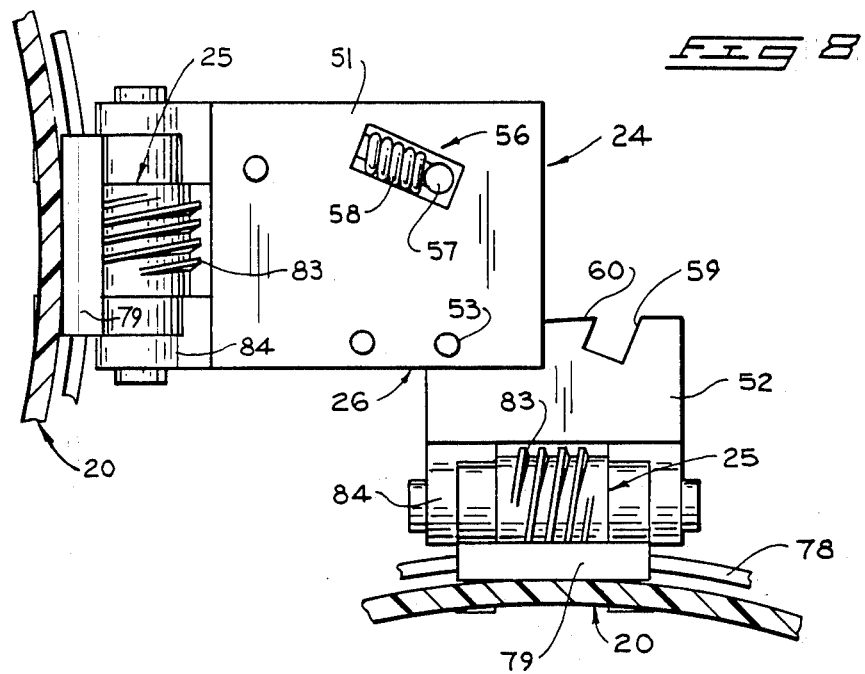
FIG. 8 is a plan view similar to FIG. 7 only showing an open position of the breakaway hinge structure shown in FIG. 7.

In compliance with the constitutional purpose of the Patent Laws "to promote the progress of science and useful arts" (Article 1, Section 8), applicants submit the following disclosure of their invention.

The present appliance is generally shown at 10 in FIG. 1 to be placed on the legs of a patient 12 for the purpose of correcting various orthopedic problems caused by incorrect or malposition of the patient's upper legs 13. For purposes of further description of the present invention, the patient's knees will be indicated by the number 14 and lower legs by the number 15.

The present appliance 10 includes two pairs of cuff members, with each pair including a first cuff member 20 for attachment to the upper leg 13 and a second cuff member 21 for attachment to the lower leg 15. The cuff members 20 and 21 of each pair are joined together by means 23, spanning the distance between the cuff members and overlapping the patient's knees 14.

The cuff pairs are joined together by a cross member generally shown at 24. The cross member 24 may be supplied with an adjustable fibular torsion means 25 that can be selectively adjusted to apply selected torsion to the upper legs 13. The cross member can also be provided with a breakaway means 26 that facilitates pivotable motion of the cuffs relative to one another between operative positions as shown in FIG. 1 and inoperative positions as shown in FIG. 2.

The first cuff members 20 are shown in substantial detail in FIGS. 1, 2, 3, and 13. They are preferably formed of a semi-rigid material such as an appropriate plastic that will retain its shape though allows some resilient bending to accommodate the patient's upper leg 13. The first cuff members 20 are of a general "U" configuration having substantially straight leg sections 28 joined by a closed curved surface 29. The straight leg sections 28 are spaced apart to receive the patient's upper legs with the closed curved surfaces 29 abutting similarly curved surfaces of the patient's leg. The cuffs may fit the patient's upper leg 13 as indicated in FIG. 1 along the back or posterior side of the thigh.

The cuffs 20 extend longitudinally between proximal ends 30 and distal ends 31. The proximal ends 30 are to be situated adjacent the patient's knee 14. The distal ends 31 will then be spaced away from the knee along the leg.

Means is provided at 32 for securing the first cuff members to the upper leg 13. Means 32 may be provided in the form of flexible straps connected to appropriate slots in the cuff members 20. Such straps may be of conventional form and have buckle or other attachments thereon for adjustment to the patient's thigh 13.

The second cuff members 21 are "U" shaped somewhat similarly to the first cuff members and may be formed of the same semi-rigid material. The second cuff members 21 may also be "U" shaped to receive the patient's lower legs 15. The cuff members 21 extend along the lower legs between proximal ends 34 to distal ends 35.

Means is supplied at 36 for releasably securing the second cuff members 21 to the users lower legs. Means 36 may simply be straps similar to those provided for the first cuff members 20, to releasably secure the cuffs 21 to the patient's lower legs 15. The straps can be fitted through appropriate slots formed through the cuff members 21 and over the patient's legs 15.

The means 23 for joining the first and second cuff members of each pair may be provided in the form of a knee hinge arrangement by which the patient's knee joints are allowed to pivot about their normal axes within prescribed angular limits. The cuff members 20 and 21 may be joined in such a manner by pivotably joined hinge bars 37 and 38 rigidly mounted to and extending in opposite directions from the proximal ends 30, 34 of the first and second cuff members. Hinge pins 39 join the bars 37 and 38 for free pivotable motion about axes that can be positioned to coincide substantially with the knee axes of the patient.

A stop means 40 is provided along the hinges bars 37 and 38 to limit pivotable motion of the cuff members relative to one another about the knee hinges axes. The stop means 40 may be comprised of an abutment 41 on one of the hinge bars for each cuff pair and a stop surface 42 is situated on the remaining bar pivoted thereto (FIGS. 4 and 5). The stop surfaces 42 are positioned angularly in relation to the associated hinge pins 39 such that pivotable motion of the first and second cuff members of each pair is limited to an arch with an inclusive angle between 70° (FIG. 4) and 150° (FIG. 5). This angular span or arch is indicated in FIG. 4 and 5 to show the extreme allowable limits of pivotable movement for the cuffs. This motion is limited at the 150° position in order to hold the patient's leg in a somewhat flexed orientation. The legs are held in this slightly flexed orientation to gain purchase for the cuff pairs in the application of torsion as applied to the adjustable fibular torsion means 25 briefly discussed above. The arc through which the cuff members will swing, however, will allow a reasonable amount of free motion for the patient's legs without interfering with the continuous application of torsion when the appliance is set in the operative position as shown in FIG. 1.

The knee hinge axes defined by hinge pins 39 may be selectively adjusted to accommodate different size legs. This adjustment is provided through an axis adjusting means 45 on each cuff 21 to place the associated hinge pin axis substantially coaxially with the normal knee hinge axis of the associated leg. The axis adjusting means 45 may be comprised in cutout areas 46 provided in at least one of the cuff members in each pair and an adjustable length strap 47 spanning the cutout area 46. The adjustable length straps 47 can be adjusted to shift the associated cuff end 30 and hinge bar rigidly mounted thereto into a proper orientation in relation to the patient's knees 14.

As shown in the drawings, the cutout areas 46 are provided on the first cuff members 20 adjacent the proximal ends 30 thereof. It is conceivable, however, that the cutout areas and straps 47 could as well been provided on the second cuff members 21 or, alternatively, to both cuff members of each pair.

The adjustment provided by the cutouts 46 and straps 47 is completed simply by changing the length of the adjustable straps 47. This increases or decreases the "depth" of the associated cuff member at its proximal end. Therefore, the straps could be tightened to adjust the knee hinge axis for persons having relatively thin legs or lengthened to accommodate heavier legs. The hinge pins 39, through this adjustment, may remain at a desired positions substantially coaxial with the patient's knee joints. This is an important adjustment since it facilitates both comfort of the patient and maintains the hinge axes in proper position with the knee so the cuffs will not shift longitudinally when the legs are flexed or extended.

The cutout areas 46 define side flanges 48 along the associated cuff members. The side flanges 48 are held securely by the straps against medial and lateral sides of the patient's leg. Actually, the flanges, as shown in FIG. 1, may substantially straddle the patient's knees and rigidly position the hinge pins 39 in relation to the knees. The flanges 48 are thus interposed between the hinges and the knee or leg surfaces to isolate the hinge action of the hinge bars 37 and 38 to protect the patient from pinching.

The breakaway hinge means 26 may be provided in several forms as indicated in the drawings. FIGS. 1, 2, and 6 through 8 indicate a first form of the hinge means; FIGS. 10 through 12 indicate another form; and FIGS. 14 through 16 indicate a third form.

Basically, the breakaway hinge means 26 is intended to facilitate pivotable motion of the cuff pairs between the operative position shown in FIG. 1 and an inoperative position shown in FIG. 2. The operative position of FIG. 1 locks the cuffs in a preselected position set by the adjustable torsion means 25 to apply prescribed torsion to the patient's legs. In the inoperative position shown in FIGS. 2 and 8, the cuff members have been moved together for ease in fitting and removing the cuffs to and from the patient's legs. This motion is allowed without affecting the torque settings adjusted through the torsion means 25 as will be understood from further discussion below.

The breakaway hinge form shown in FIGS. 1, 2, and 6 through 8 is simply comprised of first and second hinge plates 51, 52 joined by a hinge pin 53. The hinge pin 53 is situated substantially midway between the cuff pairs along an axis A—A. This axis may lie within the midsagittal plane of the patient as indicated in FIG. 1.

A detent means is generally shown at 56 for releasably locking the hinge plates 51, 52 in their operative positions. The detent means 56 may comprise a pin 57 extending through the plates and biased by a spring 58. The pin and spring are mounted to one of the hinge plates for sliding motion toward or away from a notch 59 in the remaining hinge plate. The notch 59 receives the pin to lock the hinge plates together as shown in FIGS. 6 and 7.

The pin 57 can be pulled engagement with the notch 59 to allow the plates to pivot on the pin 57 as indicated in FIGS. 2 and 8. The pin must be pulled against resistance of the spring from the slot to unlock the hinge plates. The plate 52 includes a cam surface 60 adjacent the notch 59 to cam the pin backward then allow it to spring into the notch as the cuffs are pivoted to their operative positions. The pin will snap into the notch 59 just as the hinge plates become aligned (FIG. 7) to lock the associated cuff pairs in their operative positions.

The breakaway hinge means 50 shown in FIGS. 10 through 12 involves use of opposed hinge mounting brackets 63 rotatably mounting intermeshing gear sectors 65 by pivot pins 64. The pins 64 are situated at the axes of rotation for the gear sectors and extend through the sectors and mounting brackets 63. The gear sectors 65, in turn, are mounted to the cuff pairs via the torsion adjusting means 25.

The gear sectors 65 (and attached cuff pairs) rotate simultaneously about their pivot pins 64 on parallel axes spaced substantially equi-distant from the midsagittal plane. The gear sectors assure equi-angular pivotal motion of the cuff pairs toward or away from one another between the operative and inoperative positions. They also will space the cuff members apart in the inoperative positions due to the spaced nature of the pivot pins 64. Thus, the cuff pairs can be positioned in a somewhat more accommodating orientation in the operative position to further facilitate fitting and removal of the cuff pairs.

FIGS. 11 and 12 indicate a form of the detent means 56 adapted for the gear sector arrangement. Here, the pin 57 is slidably received in appropriate opposed slots in the hinge mounting bracket 63. It also slides in an arcuate slot 67 formed through one of the gear sectors to facilitate movement thereof between the operative and inoperative postions. The notch 59 is also provided in the same gear sector, opening into the slot 67. FIG. 11 shows the pin 57 seated in the notch 59 to lock the sectors in position. Actually, the pin locks the directly associated sector (containing the notch 59) in position relative to the hinge mounting brackets 63. The gear teeth of that gear sector therefore become immovable relative to the bracket 63. These immovable teeth will then securely hold the remaining gear sector.

Figure 14:
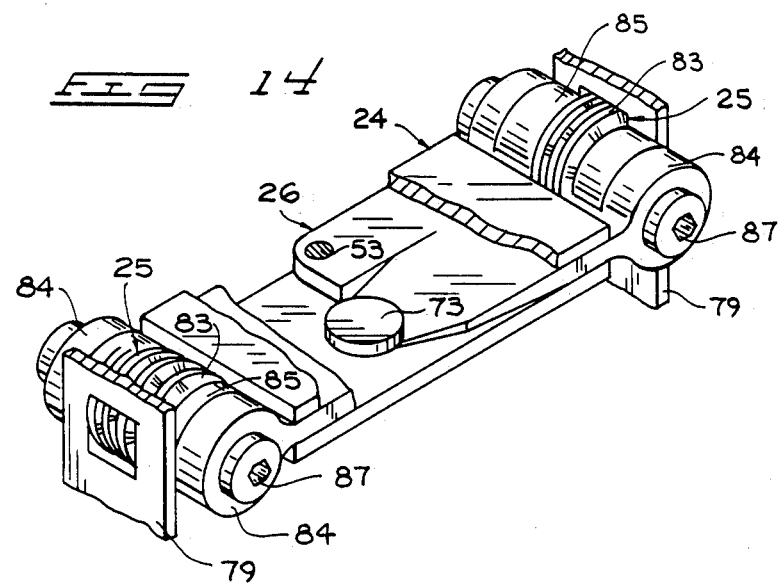
FIG. 14 is a pictorial view of a further embodiment of a breakaway mechanism for the present appliance.
Figure 15:
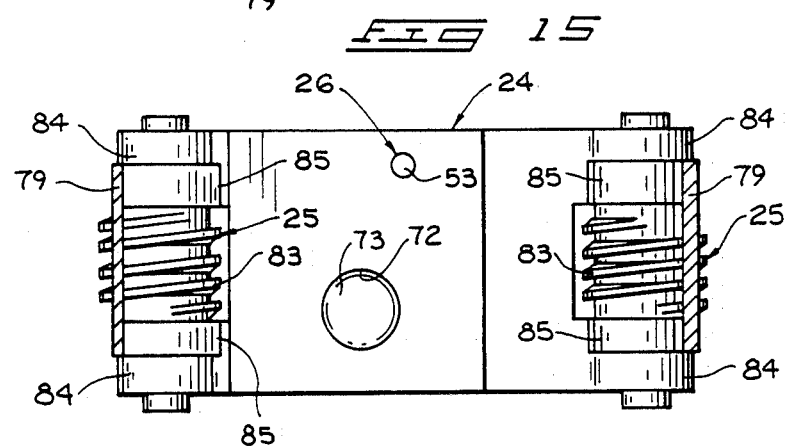
FIG. 15 is a plan view of the embodiment shown in FIG. 14.
Figure 16:
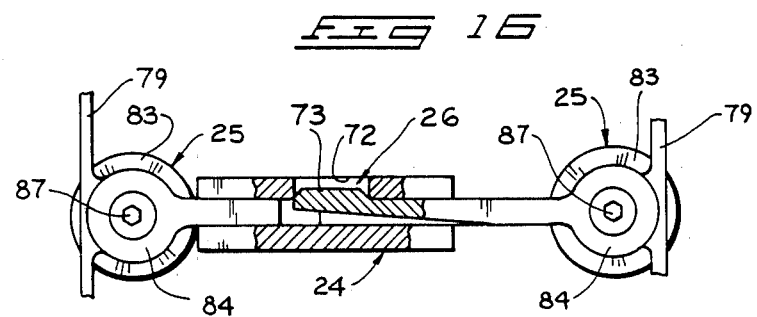
FIG. 16 is a fragmented elevation view of the breakaway mechanism shown in FIGS. 14 and 15.

FIGS. 14 through 16 indicate the third form of breakaway hinge means. In this form, one of the hinge plates includes a hole 72 spaced radially from the hinge pin 53. This hole 72 receives a spring biased button 73 formed on the remaining hinge plate. The button will snap into engagement with the hole to lock the hinge plates in their operative orientation (FIGS. 15 and 16) as the cuff pairs swing apart. The spring biased button 73 can be depressed to release the two hinge plates which will then pivot freely about the axis of the pin 57, and allow the attached cuff pairs to swing back to their inoperative positions.

The adjustable fibular torsion means 25 is provided to set the operative positions of the cuff pairs to apply selected torsional forces to the patient's legs. The position of the fibula of each leg and associated rotational axis C—C (FIG. 1) for the attached cuffs are generally indicated in FIG. 1.

The torsion adjusting means 25 is mounted to the hinge plates of the breakaway hinge means and, taken together with the hinge means 26, comprise the entire cross member 24.

Means 25 includes an arched track 78 situated on each of the cuff pairs. Preferably the track 78 is situated in a transverse plane with respect to the patient's body. Also, it is preferred that the tracks be arched in a somewhat circular orientation with the centers for the arches positioned along the respective axes C—C.

Figure 9:
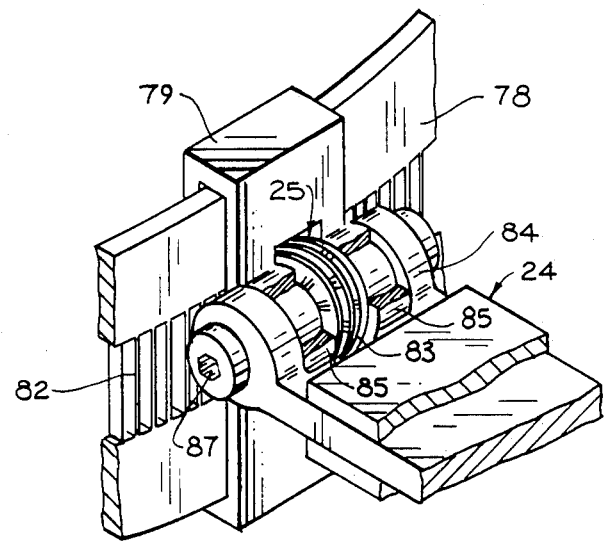
FIG. 9 is an enlarged fragmentary detailed view of a torsion adjusting mechanism for the present appliance.

Each track 78 is rigidly affixed to the cuff members and extend somewhat outwardly therefrom to receive a slide means 79 on opposite ends of the cross member 24. The slide means 79 joins the arched tracks and the cross member of the appliance for relative rotational movement about the central axes C—C of the tracks. The individual slides are shaped, as indicated in FIGS. 6 and 9 to grip the tracks and to facilitate sliding motion thereof along the track lengths.

The tracks 78 may each include an elongated gear rack 82. The cogs of the rack may be formed integrally with the tracks in the nature of slots that have been milled, punched, or otherwise formed through the track material. The cogs are positioned to be engaged by the threads of worms 83.

The worms 83 are mounted for selective rotation about parallel axes that are substantially tangential to the arcuate tracks. The worms are held for rotation by journals 84, 85 provided on hinge plates 51, 52 and slides 79. The journals rotatably hold the worms in position and, in addition, allow relative pivotal motion of the cuff pairs about parallel journal axes. These axes B—B indicated in FIG. 1 appear to converge. This is due to perspective. The axes are actually parallel.

The worms 83 include spiral flights that mesh with the gear racks 82. Rotation of the worms 83 will therefore result in corresponding relative motion of the worms and tracks in an axial direction with respect to the worm lengths. In actual use, rotation of the worms will cause rotation of the corresponding cuff pairs about their axes C—C. The worms 83 can therefore be selectively adjusted to set the desired angular position of the cuff pairs about the axes C—C in order to apply torsional forces along the patient's legs.

It is the inherent nature of the worm and rack arrangement that rotational motion of the worms will cause corresponding motion of the racks. However, this motion may not be reversed. That is, motion of the racks about axes C—C will not produce rotation of the worms. Therefore, the worms can be used to set and lock the cuff pairs in whatever angular position is selected. There is no need for set screws or locking devices along the length of the tracks, due to the mechanical relationship of the worm/rack relationship.

Each of the worms 83 may be provided with a fitting 87 for receiving an adjustment tool. As shown, a hex fitting is supplied to receive a typical "Allen" wrench. Other appropriate fittings could also be used.

The settings produced by the worms 38 may be established from time to time throughout the development or correction period. The settings produced through the worms 83 are preferably made by the attending physician or therapist. These settings will remain unaffected so long as the worms are not tampered with, due to the independent nature of the torsion adjusting means 25 and breakaway hinge means 26. The torsional settings will remain the same regardless of movement of the cuff members between their operative and inoperative positions.

The present appliance is fitted to a patient by first releasing the detent means 56 and shifting the cuff pairs to their inoperative positions as shown in FIG. 2. The cuff pairs, in this position, are directly adjacent to one another and can be easily mounted to the patient's legs. This is done by fitting the cuff members over the legs and securing the appropriate straps in position.

A check can be made at this time to determine the appropriate position of the knee hinge axes in relation to the patient's knees. If adjustment is required, the adjustable length straps 47 can be positioned to more appropriately locate the knee hinge axes of the hinge bars 37, 38 approximately coaxially with the patient's knees.

The patient's legs may be rotated to a pre-selected angular orientation following mounting of the cuff pairs. This is done simply by gently rotating the legs apart about the breakaway hinge axis. The hinge plates 51 and 52 will pivot about their axis until the pin 57 is cammed down and subsequently snaps into the notch 59. This locks the cuff pairs in their separated, operative orientations. This procedure is essentially similar with all described forms of the breakawy hinge means.

The attendant may then use an appropriate tool to turn the worms 83. Rotational motion of the worms causes the cuff pairs to rotate about their axes C—C and apply selected corrective torsional forces to the patient's legs. This is a gradual movement controlled by the speed of rotation of the worms 83. It also applies a positive torsional force due to the secure mounting of the cuff pairs. The angulation of the cuffs in each pair relative to one another is such that the cuffs will not simply slide around the patient's legs as torsion is applied, but will apply direct, positive rotational forces to the fibulas.

Comfort of the patient is maximized due to the provisions of pivot axes at the knees of the cuff pairs and at the journals 84. The knee hinge arrangements will allow the patient to flex his or her legs between the proscribed angular limits (70°-150°) while the journals 84 will allow sufficient up and down or longitudinal motion of the cuff pairs relative to one another. The patient is therefore allowed to shift positions periodically while the corrective torsional forces remain substantially the same.

The present appliance can be removed from the patient's legs without changing the preset adjustment of the torsional adjustment means 25. This is accomplished simply by releasing the appropriate detent pin or button and allowing the cuff pairs to swing together about the axis of the breakaway hinge pin or pins 53. The cuffs can then be removed while the patient assumes a natural legs-together position. The straps can be disconnected and the cuffs pulled from the patient's legs.

Later, when the appliance is again positioned on the patient's legs, the above described mounting process can be repeated without requiring that the torsional adjustment be reset. Such resetting can be accomplished periodically by the physician or therapist so no particular skill or expertise is required of the parent or the attendant in mounting or dismounting the appliance to the patient.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. An orthopedic leg appliance mountable to a patient's legs adjacent the knees, for applying rotational forces to at least one of the legs, the appliance comprising:
  first leg cuffs mountable to the patient's upper legs adjacent to the knees;
  second leg cuffs mountable to the patients lower legs;
  means interconnecting the first and second cuffs to form two cuff pairs with each cuff pair including one first cuff and one second cuff;
  a cross member joining the cuff pairs;
  breakaway hinge means on the cross member selectively operable for:
  (a) releasing the cuffs to pivot relative to one another about a midsagittal pivot axis between inoperative positions wherein the cuff pairs are positioned to facilitate application or removal of the cuffs to or from the patient's legs and operative positions wherein the cuffs are positioned to apply corrective torsional forces to at least one of the patient's legs; and
  (b) locking the cuff pairs in their operative positions; and
  adjustable torsion means on the cross member operatively engaging at least one of the cuffs for selectively rotating the one cuff to apply corrective torsion to the patient's leg on which the one cuff is mounted.

2. The orthopedic leg appliance as claimed by claim 1 wherein the breakaway hinge means is comprised of:
  a first hinge plate mounted to the first cuff of one cuff pair;
  a second hinge plate mounted to the first cuff of the remaining cuff pair;
  a hinge pin joining the first and second hinge plates for free pivotal motion about a transverse hinge axis substantially parallel to the patient's upper legs; and
  detent means between the first and second hinge plates for selectively:
  (a) locking the cuff pairs in operative positions set by the torsion adjusting means; and
  (b) unlocking the cuff pairs for free pivotal motion about the hinge axis to inoperative mounting positions facilitating mounting of the cuff pairs to a patient's legs.

3. The orthopedic leg appliance as claimed by claim 2 wherein the first and second hinge plates include first and second gear sectors respectively, intermeshing and formed about parallel axes;
  a hinge mounting bracket mounted by the hinge pin in the first hinge plate, the hinge pin being coaxial with the axis of the gear sector on the first hinge plate; and
  a second hinge pin pivotably interconnecting the second hinge plate to the hinge mounting bracket, the second hinge pin being coaxial with the axis of the second gear sector.

4. The orthopedic leg appliance as claimed by claim 2 wherein the detent means is comprised of:
  a hole formed in one of the hinge plates spaced radially from the hinge axis; and
  a spring biased button on the remaining hinge plate receivable in the hole to lock the hinge plates together about the hinge axis and yieldable to release the hinge plates to pivot freely about the hinge axis.

5. The orhtopedic leg appliance as claimed by claim 1 wherein the first cuffs are "U" shaped in cross section and wherein the adjustable torsion means is comprised of:
  a track mounted to each of the first cuffs, having an arcuate "U" shape similar to the "U" shaped cuff configuration;
  a slide on the breakaway hinge means mounted to each track for sliding motion thereon; and
  means on the slides for selectively rotating the tracks and associated cuffs relative to the breakaway hinge means.

6. The orthopedic leg appliance as claimed by claim 5 wherein the tracks include arcuate gear racks thereon and wherein the means on the slides for rotating the tracks are comprised of worms mounted to the slides in meshing engagement with the gear racks and rotatable about worm axes tangential to the arcuate gear racks, to rotate the gear racks and attached cuffs.

7. The orthopedic leg appliance as claimed by claim 6 further comprising journals on the breakaway hinge means and slides rotatably housing the worms for rotation therein about their worm axes and for allowing pivotal motion of the cuff pairs relative to the breakaway hinge means about the worm axes.

8. The orthopedic leg appliance as claimed by claim 1 wherein the means interconnecting the first and second cuffs of each cuff pair is comprised of:
  a pair of knee hinge bars extending toward one another from the first and second cuffs of each cuff pair, the bars of each cuff pair being joined by a pivot pin to allow free pivotal motion of the cuffs about a knee hinge axis; and
  stop means for limiting pivotal motion of the cuffs of each pair about the knee hinge axis between full flexed positions wherein the inclusive angle between the hinge bars is approximately 70° and partially extended positions wherein the inclusive angle between the hinge bars is approximately 150°.

9. The orthopedic appliance as claimed by claim 8 further comprising:
  axis adjusting means on one of the cuffs in each pair for selectively positioning the knee hinge axis substantially coaxially with the knee axis of the patient's leg.

10. The orthopedic appliance as claimed by claim 9 wherein at least one of the cuffs of each pair is "U" shaped with free ends spaced apart to straddle the patient's leg adjacent the knee and a closed curved end of the "U" shape to be received flush against the leg; and
  wherein the axis adjusting means includes a cutout area along the closed curved surface of the one cuff of each pair, defining side flanges positionable by the one cuff on medial and lateral surfaces of the leg, and
  an adjustable length strap mounted to the side flanges and extending across the cutout area.

11. The orthopedic appliance as claimed by claim 10 wherein the cutout area and adjustable strap are on the first leg cuffs.

12. The orthopedic appliance as claimed by claim 10 wherein the cuffs include proximal ends to be situated adjacent the patient's knees and distal ends spaced along the legs from the proximal ends, and wherein the cutout area of the one cuff of each pair is located along the proximal cuff end.

13. A knee hinge assembly mountable to the upper and lower leg of a patient, adjacent the patient's knee joint, comprising:
  a first cuff member of semi-rigid material having a "U" shaped cross section with legs of the "U"

shape spaced apart to straddle the upper leg adjacent the knee and a closed curved surface of the "U" shape joining the legs of the "U" shape; to be received flush against the upper leg;

first means on the first cuff member for securing the first cuff member to the upper leg with the closed curved surface flush against the leg;

a second cuff member of semi-rigid material shaped to be received on the patient's lower leg adjacent the knee;

second means on the second cuff member for securing the second cuff mebmer to the lower leg adjacent the knee;

knee hinge means interconnecting the first and second cuff members for pivotal movement about a knee hinge axis through a prescribed angle; and axis adjusting means on one of the cuff members extending across the closed curved section of the "U" shaped cross section thereof for selectively positioning the hinge axis of the knee hinge means forward or backwardly to approximatey match the knee axis of a patient's leg.

14. The knee hinge assembly as claimed by claim 13 wherein the knee hinge means is comprised of:
a pair of knee hinge bars extending toward one another from the first and second cuffs of each cuff pair, the bars of each cuff pair being joined by a pivot pin to allow free pivotal motion of the cuffs about a knee hinge axis; and stop means for limiting pivotal motion of the cuffs of each pair about the knee hinge axis between full flexed positions wherein the inclusive angle between the hinge bars is approximately 70° and partially extended positions wherein the inclusive angle between the hinge bars is approximately 150°.

15. The knee hinge assembly as claimed by claim 13 wherein the axis adjusting means includes:
a cutout area along the closed curved surface of one cuff member, defining opposed side flanges positionable by the one cuff on medial and lateral surfaces of the patient's leg; and an adjustable length strap mounted to the side flanges and extending across the cutout area.

16. The knee hinge assembly as claimed by claim 15 wherein the cutout and adjustable length strap are on the first cuff member at an end thereof adjacent the knee hinge means.

17. The knee hinge assembly as claimed by claim 15 wherein the cutout and adjustable length strap are situated on the one cuff member at an end thereof adjacent the knee hinge means.

18. A torsion adjustment on an orthopedic leg appliance having upper and lower arcuate cuffs mountable to a patient's leg and separated by a cross member, the adjustment comprising:
an arched track affixed to one of the arcuate cuffs to extend along a substantially transverse plane in relation to the patient's leg at least partially around the one arcuate cuff and having a center axis positionable by the one arcuate cuff approximately coaxial with the patient's leg.;

slide means joining the arched track and the cross member of the orthopedic appliance for relative rotational movement about the center axis of the track; and adjustment means between the slide means and track operable against the arched track to forcibly rotate the arched track and attached cuff about the center axis relative to the cross member, to a selected position and to lock the track and attached cuff in the selected position in relation to the cross member.

19. The torsion adjustment as claimed by claim 18 wherein the arcuate track includes a gear rack extending along the arcuate configuration of the cuff; and
wherein the adjustment means is comprised of a worm on the cross member rotatable on the cross member about a worm axis tangential to the arcuate track and having worm teeth engaging the gear rack.

20. The torsion adjustment as claimed by claim 19 wherein the cross member and slide are hingedly mounted to the worm for free pivotal motion about the worm axis.

* * * * *